(12) United States Patent
Casper et al.

(10) Patent No.: US 7,078,394 B2
(45) Date of Patent: Jul. 18, 2006

(54) LOW DOSE ESTROGEN INTERRUPTED HORMONE REPLACEMENT THERAPY

(75) Inventors: Robert F. Casper, Toronto (CA); Gary A. Shangold, Califon, NJ (US); Militza K. Ausmanas, Lake Forest, IL (US)

(73) Assignee: Duramed Pharmaceuticals, Inc., Pomona, NY (US)

( * ) Notice: Subject to any disclaimer, the term of this patent is extended or adjusted under 35 U.S.C. 154(b) by 0 days.

(21) Appl. No.: 10/806,613

(22) Filed: Mar. 22, 2004

(65) Prior Publication Data

US 2004/0180867 A1    Sep. 16, 2004

Related U.S. Application Data

(63) Continuation of application No. 10/134,455, filed on Apr. 30, 2002, now Pat. No. 6,747,019, which is a continuation of application No. 09/538,485, filed on Mar. 30, 2000, now abandoned.

(60) Provisional application No. 60/126,970, filed on Mar. 30, 1999.

(51) Int. Cl.
*A61K 31/56* (2006.01)

(52) U.S. Cl. .................................. 514/170
(58) Field of Classification Search ................ 514/170
See application file for complete search history.

(56) References Cited

U.S. PATENT DOCUMENTS

| | | | |
|---|---|---|---|
| 4,957,119 A | 9/1990 | De Nijs | 128/832 |
| 5,088,505 A | 2/1992 | De Nijs | 128/830 |
| 5,108,995 A | 4/1992 | Casper | 514/170 |
| 5,256,421 A | 10/1993 | Casper | 514/170 |
| 5,276,022 A | 1/1994 | Casper | 514/170 |
| 5,382,573 A | 1/1995 | Casper | 514/170 |
| 5,422,119 A | 6/1995 | Casper | 514/170 |
| 5,585,370 A | 12/1996 | Casper | 514/170 |
| 5,633,242 A | 5/1997 | Oettel et al. | 514/170 |
| 6,133,251 A | 10/2000 | Dittgen et al. | 514/170 |

FOREIGN PATENT DOCUMENTS

| | | |
|---|---|---|
| DE | 44 29 374 | 2/1996 |
| EP | 0 275 716 | 7/1988 |
| EP | 0 309 263 | 3/1989 |
| EP | 0 770 388 | 5/1997 |
| WO | WO 97/11680 | 4/1997 |
| WO | WO 98/37897 | 9/1998 |

OTHER PUBLICATIONS

Lobo, et al., "A novel intermittent regimen of norgestimate to preserve the beneficial effects of 17β-estradiol on lipid and lipoprotein profiles," Am. J. of Obstet. & Gynecol., vol. 182, No. 1, Part 1, Jan. 2000, pp. 41-49 (XP-000900454).

Sulak, et al., "Efficacy and Safety of a Constant-Estrogen, Pulsed-Progestin Regimen in Hormone Replacement Therapy," Int'l. Journal of Fertility and Women's Medicine, Nov.-Dec. 1999, pp. 286-196 (XP-000934379).

Vanin, et al., "Lumbar vertebral density and mechanical properties in aged ovariectomized rats treated with estrogen and norethindrone or norgestimate," Am. J. Obstet. & Gynecol., vol. 173, No. 5, Nov. 1995, pp. 1491-1498 (XP-000934383).

Christin-Matrie, et al., "Perceptives de la contraception," La Revue du Practicien, 1995, pp. 2449-2453 (English abstract on p. 2453 (last page)).

*Primary Examiner*—Barbara P. Badio
(74) *Attorney, Agent, or Firm*—Sterne, Kessler, Goldstein & Fox P.L.L.C.

(57) ABSTRACT

A hormone replacement therapy, comprising a plurality of daily doses of a pharmaceutical preparation, the doses being administered continuously and consecutively in alternating phases of three daily doses, a relatively dominant estrogenic activity phase comprising three daily doses of a substance exhibiting estrogenic activity equivalent to about 1 mg per day of 17β-estradiol per day, and a relatively dominant progestagenic activity phase of a combination of a substance exhibiting estrogenic activity equivalent to about 1 mg per day of 17β-estradiol and a substance exhibiting progestogenic activity equivalent to about 90 μg per day of norgestimate.

4 Claims, 1 Drawing Sheet

LOW DOSE ESTROGEN INTERRUPTED HORMONE REPLACEMENT THERAPY

CROSS REFERENCE TO RELATED APPLICATIONS

This application is a continuation of, and claims priority to U.S. application Ser. No. 10/134,455, which was filed on Apr. 30, 2002 now U.S. Pat. No. 6,747,019. This application is a continuation of and claims benefit of U.S. application Ser. No. 09/538,485 (abandoned), which was filed on Mar. 30, 2000. Lastly, this application claims the benefit of U.S. Provisional Application No. 60/126,970, which was filed on Mar. 30, 1999.

BACKGROUND OF THE INVENTION

1. Field of the Invention

The present invention relates to hormone. replacement therapy (HRT) for administration to menopausal or castrate women. More specifically, the present invention relates to a hormone replacement therapy regimen comprising a specific dosage combination that includes a reduced amount of estrogen, which provides a reduced risk of cancer, while providing a regimen with vasomotor symptom relief that is usually only available at higher estrogen levels.

1. Background Art

There are a number of patents relating to hormone replacement therapy and many different formulations available in the marketplace. Many formulations involve the administration of continuous estrogen and progestogen, while other regimens can be characterized as interrupted or cyclophasic. Examples of patents covering interrupted regimens include Robert F. Casper's U.S. Pat. No. 5,108,995 issued Aug. 28, 1992, for a method of HRT; U.S. Pat. No. 5,256,421 issued Oct. 26, 1993 for an HRT method; U.S. Pat. No. 5,422,119 issued Jun. 6, 1995 for a transdermal HRT method, preparation and package; and U.S. Pat. No. 5,382,573 issued Jan. 17, 1995, which relates to an HRT preparation and package. Casper is also the holder of U.S. Pat. No. 5,276,022 issued Jan. 4, 1994 and U.S. Pat. No. 5,585,370 issued Dec. 17, 1996 both of which relate to contraceptive therapy. The disclosures of all of these patents are incorporated herein by reference.

The Casper hormone replacement therapy (HRT) and hence the cyclophasic regimens disclosed by Casper seek to induce higher levels of progestogen and estrogen receptors by an estrogen-induced increase in receptor production. The greater concentration of steroid receptors increases the sensitivity of the target organs to progestogen and estrogen and allows the use of lower doses of exogenous steroids. The cyclophasic or interrupted regimens of Casper upregulate the estrogen and progestogen receptors in an estrogen-dominant phase and then down-regulate the same receptors in a progestogen-dominant phase. In both phases of the Casper regimen, the estrogen dose is constant while the progestogen dose is varied to produce relatively progestogen-dominant or estrogen-dominant effects. These alternating phases continue without interruption in the Casper HRT regimen.

Hot flashes or flushes occur in about 75 percent of menopausal women. The flushes may begin in the perimenopausal period when relative estrogen deficiency occurs together with cycle irregularity secondary to anovulation, but they usually begin during or after the menopause. Hot flushes typically begin as a sudden sensation of heat centered on the face and upper chest that rapidly becomes generalized. The sensation of heat lasts between two and four minutes, is frequently associated with profuse perspiration and occasionally palpitations, and is often followed by chills and shivering [Casper, R F,. Yen, S S C. *Neuroendocrinology of menopausal flushes: An hypothesis of flush mechanism. Clin Endocrinol* 1985; 22:293].

Hot flushes usually occur several times per day, although the range may be from only one or two each day to as many as one per hour during the day and night. Flushes cause arousal from sleep, leading to sleep disturbances. In addition, many women have profuse perspiration, which can be embarrassing in social situations.

The cause of hot flushes is unknown. They are thought to be due to thermoregulatory dysfunction, initiated at the level of the hypothalamus by estrogen withdrawal [ibid.] Evidence for central mediation of the changes in temperature comes from studies demonstrating that hot flushes occur simultaneously with pulses of luteinizing hormone [Casper, R F, Yen, S S C, Wilkes, M M. *Menopausal flushes: A neuroendocrine link with pulsatile luteinizing hormone secretion. Science* 1979; 205:823 and Tataryn, I V, Meldrum, D R, Lu, K H, et al. *LH, FSH and skin temperature during the menopausal hot flash. J Clin Endocrinol Metab* 1979; 49:152].

A speculative mechanism for the initiation of hot flushes is endogenous opioid peptide withdrawal. Estrogen increases central opioid peptide activity, while menopause appears to be associated with decreased or absent endogenous central opioid activity [Reid, R L, Quigley, M E, Yen, S S. *The disappearance of opiodidergic regulation of gonadotropin secretion in postmenopausal women. J Clin Endocrinol Metab* 1983; 573107].

Whatever the cause of hot flushes, the most effective way known to prevent or treat them in women with estrogen deficiency is to administer estrogen.

In women who have not had a hysterectomy, estrogen should always be given in combination with a progestogen, to prevent the occurrence of endometrial hyperplasia and associated malignancies of the endometrium. Estrogen-progestogen therapy also is more effective than estrogen alone in ameliorating hot flushes, possibly because progestogen also increases central opioid peptide activity [Casper, R F, Alapin-Rubillowicz, S J. *Progestogen* 15 *increases endogenous opioid peptide activity in postmenopausal women. J Clin Endocrinol Metab* 1985; 60:34].

Progestogen administration alone can inhibit gonadotropin secretion, increase hypothalamic endogenous opioid peptide activity [Casper, R F, Alapin Rubillowicz, S J. *Progestogen increases endogenous opioid peptide activity in postmenopausal women. J Clin Endocrinol Metab* 1985; 60:34], and ameliorate hot flashes Schiff, I. *The effects of progestogen on vasomotor flushes. J Rep rod Med* 1982; 27(Suppl):498]. As an example, megestrol acetate (at a dose of 20 to 80 mg/day) decreases the frequency of hot flushes by 85 percent (versus 21 percent with placebo) [Loprinrzi, C L, Michalak,. J C, Quella, S K, et al. *Megestrol 25 acetate for the prevention of hot flashes. N Engl J Med* 1994; 331:347]. Other progestogens such as norethindrone acetate (10 mg daily) are also effective.

The bothersome symptoms of hot flushes are the most frequent reason for women to seek hormone replacement therapy. The improvement in hot flushes leads to long term utilization of hormone replacement therapy with many additional benefits of such use including a 50% reduction in heart disease, prevention of osteoporosis, and perhaps, as new evidence indicates, prevention of Alzheimer's disease. At the present time, the major controversial area concerning the risks of hormone replacement therapy involves breast cancer. It is believed, but not proven, that the risk of breast cancer in women taking hormone replacement therapy is related to the dose of estrogen exposure over time.

Despite substantial efforts made to date, there remains a need for improved HRT regimens that minimize estrogen exposure, while effectively relieving symptoms such as hot flushes.

SUMMARY OF THE INVENTION

It has now been discovered that a selected dosage regimen within the broad class proposed in the aforementioned US Patents, provides unexpected benefits that are of major significance for the patient.

The remarkable finding of the regimen is that maximum symptom relief, in particular hot flushes, is obtained with the regimen and this relief is equivalent to that for a regimen of the same type where the estrogen level is 100 percent higher. It was unexpected that symptom relief would be the same for both estrogen levels in this type of regimen.

The advantage of the present regimen over those of the same class with higher estrogen levels is that it offers an increased margin of safety because of its lower estrogen level, while providing the same symptom relief.

The regimen of the present invention was also compared with a known HRT regimen sold under the brand names KLIOGEST® and KLIOSEM® and known for its effective symptom relief. This known product contains 100 percent higher estrogen than the present formulation. Symptom relief was equivalent in both regimens.

The present invention provides, in one aspect, a pharmaceutical preparation for administration to a female in need of hormone replacement therapy, comprising a plurality of doses for consecutive administration in alternating phases, the phases consisting of a relatively dominant estrogenic activity phase comprising three daily doses or an equivalent thereof, of a substance exhibiting estrogenic activity equivalent to about 1 mg per day of 17β-estradiol, and a relatively dominant progestogenic activity phase comprising three daily doses or an equivalent thereof, of a combination of a substance exhibiting estrogenic activity equivalent to about 1 mg per day of 17β-estradiol and a substance exhibiting progestogenic activity equivalent to about 90 µg per day of norgestimate.

In a more preferred form of the pharmaceutical preparation of the invention, there is provided a pharmaceutical preparation for administration to a female in need of hormone replacement therapy comprising a plurality of daily doses for consecutive administration, the doses being administered consecutively in alternating phases, the phases comprising a relatively dominant estrogenic activity phase comprising three consecutive daily doses of a substance exhibiting estrogenic activity equivalent to about 1 mg per day of 17β-estradiol, and a relatively dominant progestogenic activity phase comprising three consecutive daily doses of a combination of a substance exhibiting estrogenic activity equivalent to about 1 mg per day of 17β-estradiol and a substance exhibiting progestogenic activity equivalent to about 90 µg per day of norgestimate.

In another aspect of the invention, there is provided a package containing a pharmaceutical preparation for administration to a female in need of hormone replacement therapy, comprising a plurality of doses for consecutive administration arranged in alternating phases, the phases consisting of a relatively dominant estrogenic activity phase comprising three daily doses or an equivalent thereof, of a substance exhibiting estrogenic activity equivalent to about 1 mg per day of 17β-estradiol, and a relatively dominant progestogenic activity phase comprising three daily doses or an equivalent thereof, of a combination of a substance exhibiting estrogenic activity equivalent to about 1 mg per day of 17β-estradiol and a substance exhibiting progestogenic activity equivalent to about 90 µg per day of norgestimate.

In a more preferred form of the pharmaceutical package of the invention, there is provided a pharmaceutical package containing a pharmaceutical regimen for administration to a female in need of hormone replacement therapy, the doses being arranged for consecutive administration in alternating phases, the phases consisting of a relatively dominant estrogenic activity phase comprising three consecutive daily doses of a substance exhibiting estrogenic activity equivalent to about 1 mg per day of 17β-estradiol, and a relatively dominant progestogenic activity phase comprising three consecutive daily doses of a combination of a substance exhibiting estrogenic activity equivalent to about 1 mg per day of 17β-estradiol and a substance exhibiting progestogenic activity equivalent to about 90 µg per day of norgestimate.

In yet another aspect the invention provides a method of treating a female in need of hormone replacement therapy comprising administering to said female a pharmaceutical regimen comprising a plurality of doses arranged in alternating phases, the phases comprising a relatively dominant estrogenic activity phase comprising three daily doses or an equivalent thereof, of a substance exhibiting estrogenic activity equivalent to about 1 mg per day of 17β-estradiol, and a relatively dominant progestogenic activity phase comprising three daily doses or an equivalent thereof, of a combination of a substance exhibiting estrogenic activity equivalent to about 1 mg per day of 17β-estradiol and a substance exhibiting progestogenic activity equivalent to about 90 µg per day of norgestimate.

In yet another aspect the invention provides a use of an estrogenically active substance and a progestogenically active substance in the preparation of a medicament, characterized in that the medicament is for hormone replacement therapy for administration to a female in need of such therapy, the medicament comprising a plurality of doses for consecutive administration in alternating phases the phases consisting of a relatively dominant estrogenic activity phase comprising three daily doses or an equivalent thereof, of a substance exhibiting estrogenic activity equivalent to about 1 mg per day of 17β-estradiol, and a relatively dominant progestogenic activity phase comprising three daily doses or an equivalent thereof, of a combination of a substance exhibiting estrogenic activity equivalent to about 1 mg per day of 17β-estradiol and a substance exhibiting progestogenic activity equivalent to about 90 µg per day of norgestimate.

In a preferred form of the invention there is provided a use of an estrogenically active substance and a progestogenically active substance in the preparation of a medicament, characterized in that the medicament is for hormone replacement therapy for administration to a female in need of such therapy, the medicament comprising a plurality of daily doses for consecutive administration in alternating phases, the phases consisting of a relatively dominant estrogenic activity phase comprising three consecutive daily doses of a substance exhibiting estrogenic. activity equivalent to about 1 mg per day of 17β-estradiol, and a relatively dominant progestogenic activity phase comprising three consecutive daily doses of a combination of a substance exhibiting estrogenic activity equivalent to about 1 mg per day of 17β-estradiol and a substance exhibiting progestogenic activity equivalent to about 90 μg per day of norgestimate.

DETAILED DESCRIPTION OF THE INVENTION

In a preferred form of all aspects of the invention, the substance exhibiting progestogenic activity is selected on the basis that it binds to progestin receptors, demonstrates poor affinity for androgen receptors and has a lack of affinity for sex-hormone-binding globulin (SHBG).

In its most preferred form, the invention provides a therapy or regimen in which the three daily doses in the relatively dominant estrogenic activity phase comprise about 1 mg per day of 17β-estradiol, and in the relatively dominant progestogenic activity phase comprise about 1 mg per day of 17β-estradiol and about 90 μg per day of norgestimate.

Generally the formulation of the invention will consist of a single oral tablet taken once daily. On days one through three of therapy, the tablet contains 17β-estradiol. On days four through six of therapy, the tablet contains both 1.0 mg. 17β-estradiol and 90 μg or 0.09 mg of norgestimate. This unique regimen consisting of a pattern of three days of 17β-estradiol only followed by three days of 17β-estradiol plus norgestimate is repeated continuously throughout therapy.

Definitions

A female in need of hormone replacement therapy

Generally this would include a female of child bearing age or older in whom ovarian estrogen and progesterone production has been interrupted either because of natural menopause; surgical, radiation, or chemical ovarian ablation or extirpation or premature ovarian failure.

a relatively dominant estrogenic activity phase a relatively dominant progestogenic activity phase One may start the regimen with either phase, although the relatively dominant estrogenic activity phase is the preferred starting phase.

The word relative defines the activity of a phase with respect to any 5 immediately preceding phase and any immediately following phase.

The only activity of the phase is the estrogenic activity and therefore it is dominant in this phase, and this activity is relative to the other estrogenic activity of the phase where a progestogenically active substance is present also.

In the relatively dominant progestogenic activity phase the dominant hormone activity is the progestogenic activity, and again this activity in this phase is dominant relative to its activity in the other phase.

In the relatively dominant estrogenic activity phase, the estrogen stimulates endometrial growth and progestogen receptors. Consequently, the endometrium is more sensitive to subsequent progestogen activity that limits growth by decreasing estrogen receptors and increasing 17β-hydroxysteroid dehydrogenase. Interaction of progestogen in the second relatively dominant estrogenic activity phase with progestogen receptors induces secretory changes in the endometrium, which results in a denser stroma and endometrial stability. A return to relatively dominant estrogenic activity then again stimulates estrogen and progestogen receptors and renews endometrial sensitivity to progestogen. This push/pull activity keeps endometrial activity within a low range depending on the number of days of estrogenic and progestogenic activity [see Cameron, Sharon T., et al, Continuous transdermal oestrogen and interrupted progestogen as a novel bleed-free regimen of hormone replacement therapy for postmenopausal women, British Journal of Obstetrics and Gynaecology, October 1997, Vol. 104, pp. 1184–1190]. In this instance, the relatively dominant estrogenic activity phase lengths that have been found to maximize this push/pull activity are three days for each relatively dominant estrogenic activity phase. a substance exhibiting estrogenic activity and a substance exhibiting progestogenic activity Any substance that exhibits appropriate. estrogenic activity may be used in the present invention. As indicated the preferred estrogen is 17β-estradiol. Other suitable estrogens include 17α-ethinylestradiol, esters and ethers of 17α-ethinylestradiol such as, for example, 17α-ethinylestradiol 17α-dimethylamino propionate, 17α-ethinylestradiol 3-cyclopentyl ether (quienestrol) and 17α ethinylestradiol 3-methyl ether (mestranol). Natural estrogens such as estrone, estrone sulfate, estrone sulfate piperazine salt, estradiol and estriol, and their esters, as well as the synthetic estrogens, may also be employed. The selection of the estrogen and the dose level will generally follow from the literature, which is well known to the person skilled in the art. The dose level is dependent on the cyclophasic regimen. The discussion that follows about the selection of a progestogen and its dose level may be used as a guide in the selection of the estrogen.

The preferred progestogen is norgestimate. Norgestimate is also known under its chemical name D-17β-acetoxy-B-ethyl-17α ethinyl-gon-4-en-3-one oxime. While other progestogens may be used in place of norgestimate, in selecting a suitable progestogen, and in particular norgestimate, selection criteria include degree of affinity for progestogen receptor, absence of affinity for androgen receptor and whether the progestogen displaced androgen from human sex-hormone-binding globulin (SHBG) [see Phillips, Audrey et al., Preclinical evaluation of norgestimate, a progestin with minimal androgenic activity, Am J Obstet Gynecology, October 1992, October 1992, Volume 167, Number 4, Part 2, pp. 1191–1196]. In the case of norgestimate, it binds to progestin receptors, it demonstrates very poor affinity for androgen receptors and it has a lack of affinity for SHBG. All of these effects make it similar to natural progesterone.

Other progestogens may be employed in the present therapy regimen as long as they meet the criteria set forth above for the selection of norgestimate. In essence, the progestogen must have a profile that is similar to norgestimate. Possible choices of those progestogens that meet these requirements include desogestrel, dydrogesterone, medroxyprogesterone acetate, norethynodrel, cyproterone acetate, chlormadinone acetate, magestrol acetate, 17 D-acetyl norgestimate, dienogest, trimegestone, drosperinone and nomagestrel. Examples of progestogens that do not have a suitable profile include norethindrone and norgestrel. The literature contains descriptions of numerous progestogens and based on the criteria set out above, the person skilled in the art may make a suitable choice.

As stated the preferred dose for norgestimate is about 90 µg. Equivalent doses for other progestogens may be determined by the person skilled in the art by reference to the literature, for example the standard text *Treatment of the Menopausal Woman, Basic and Clinical Aspects,* Ed. Lobo, Rogerio A., Raven Press, New York, pp73–80. Dosage selection is made with reference to hormone potency and the nature of the regimen, which is cyclophasic and does allow for lower levels of hormones. Examples of suitable equivalent doses include about 54 µg/day of desogestrel, about 180 µg/day of 3-keto-desogestrel, about 90 µg/day of 17D-acetyl norgestimate, about 180 µg/day of cyproterone acetate, about 720 µg/day of dienogest, about 1080 µg/day of drosperinone and about 27 µg/day of gestogen. When making a choice of dose level, it would be a matter of routine experimentation for the person skilled in the art to take the equivalent dose level in the selected hormone and then to test a few doses around that level in order to refine the dose level three daily doses or an equivalent thereof.

The daily doses of the present invention may be administered in any convenient form Preferred, as set out earlier is a single daily tablet, but any other suitable form may be employed. The single table is preferred as it reduces the likelihood that the patient will get confused. The words "an equivalent thereof" are meant to cover administrative forms that do not comprise daily doses, for example a transdermal form.

Generally speaking, the formulations are prepared according to conventionally known procedures in accordance with the desired method of administration. Different amounts of the active ingredients may be required in different types of formulations but it is essential that the amount of estrogenically active substance and progestationally active substance be selected so as to provide the dose equivalency for the regimen as described above. The percentage of active ingredients may vary according to the potency of the hormone, the delivery system or method of administration and is chosen in accordance with conventional methods known in the art.

The estrogen and progestogen compositions can be administered by way of any art recognized means as practiced in the pharmaceutical arts. For example, the estrogen and progestogen alone or in combination may be so formulated so that it can be administered orally, via a skin patch for transdermal absorption, by intramuscular injection, contained within an inert matrix which is implanted within the body and in a depot state, or intravaginally in a matrix that slowly releases the active compositions (such implants are taught for example in U.S. Pat. Nos. 4,957,119 and 5,088,505).

Pharmaceutical compositions containing compounds of the invention may further comprise pharmaceutically acceptable carriers and be in either solid or liquid form. Solid preparations include powders, tablets, dispersible granules, capsules, etc. The carrier may also be one or more substances, which act as diluents, flavoring agents, solubilizers, lubricants, suspending agents, binders, or tablet disintegrating agents as well as encapsulating materials. Suitable carriers include magnesium carbonate, magnesium stearate, talc,. lactose, sugar, peptin, dextrin, starch, methylcellulose; sodium carboxylmethylcellulose, and the like. Liquid form preparations include solutions, which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Aqueous solutions for oral administration can be prepared by dissolving the active compound in water and adding suitable flavorants, coloring agents, stabilizers and thickening agents as required. Aqueous suspensions for oral use can be made by dispersing the active component in water together with a viscous material such as a natural or synthetic gum, methylcellulose, sodium carboxymethyl-cellulose, and other suspending agents known to the pharmaceutical formulation art. Other solid dosage forms include topical dosage forms which include solutions, powders, fluid emulsions, fluid suspensions, semi-solids, ointments, pastes, creams, gels or jellies and foams; and parenteral dosage forms which include solutions, suspensions, emulsions or dry powder comprising an effective amount of estrogen or estrogen and progestogen as taught in this invention.

Various conventional techniques for preparing pharmaceutical compositions including solutions, suspensions, tablets or caplets can be employed, as would be known to those skilled in the art and as is disclosed for example by Remington's Pharmaceutical Sciences, Mack Publishing Co., Part 8, Chapters 76–93, Pharmaceutical Preparations and Their Manufacture, pp. 1409–1677 (1985).

The pharmaceutical formulations may be provided in kit form containing preferably multiples of three unit dosages, each constituting a relatively dominant estrogenic activity phase and in a suitable form, for example, caplets or tablets. The kit may comprise a dial package or a foil strip as is well known in the art. The kit would typically contain an even number of doses for each phase arranged in an even number of relatively dominant estrogenic activity phases. Thus the unit dosages would be arranged in each package in multiples of six so that an even number of phases would be present in each package.

The term "unit dosage form" as used herein refers to physically discrete units suitable as unit dosages, each unit containing a predetermined quantity of active ingredient calculated to produce the desired therapeutic effect in association with the required pharmaceutical carrier. The term "doses" as used herein broadly encompasses the term unit dosage form or dosage units as well as continuous dosing of compositions by depot or other methods. a combined preparation This term is meant to indicate that the therapy or formulation is meant to comprise both an estrogenically active substance and a progestogenically active substance. Only the relatively dominant progestogenic activity phase involves both substances delivered in combination.

Consecutively

Generally hormone replacement therapy is administered on a daily basis, every day to a patient. This is the case in the present invention, but there may be instances where hormone free days could be desirable. In such a case, dosages containing placebo or any other hormone-free agent may be included in the regimen. Examples of suitable alternative hormone-free agents include vitamins and/or iron supplements. It should be noted that the phases are consecutively administered to the patient.

The active ingredients are usually compounded with the chosen carrier and in for example the case of a tablet form, placed in a tablet molding apparatus to form the tablets which are subsequently packaged in accordance with the chosen regimen.

In the oral form of the formulation, the package would have the daily dosages arranged for proper sequential administration. Data indications may be provided on the packaging. The packaging may be a tube or box or a strip. The box may be circular, square, or otherwise shaped with the tablets for example being accommodated separately therein for ease of administration. Date indications may appear adjacent each tablet corresponding with the days on which each tablet is to be taken. Some indication of the sequence in which the tablets are to be taken preferably appears on the packaging regardless of its form.

The invention will now be illustrated by an exemplary study involving the method of the invention. The examples are not intended to be limiting of the scope of the present invention. They are to be read in conjunction with the detailed and general description above, to provide further understanding of the invention and to outline a protocol for carrying out the methods of the invention for HRT in climacteric, perimenopausal and postmenopausal women.

EXAMPLE

In a randomized parallel group multi-center, study performed by the R.W. Johnson Pharmaceutical Research Institute, three different hormonal replacement regimens were compared with respect to effects on menopausal symptoms, on bleeding patterns and on lipid and carbohydrate metabolism. A major endpoint in terms of menopausal symptoms and subsequent patient acceptance of treatment was the effectiveness of each regimen in alleviating hot flushes.

In the multicenter trial, the regimen of the present invention (containing 1 mg of estradiol and 90 μg of norgestimate) was compared with another interrupted progestogen regimen that is derived from the previously referenced Casper U.S. patents, and contained 2 mg of estradiol and 180 μg of norgestimate) and to a reference preparation containing 2 mg of estradiol and 1 mg of norethindrone acetate, which is currently marketed in Europe under the trademark KLIOGEST® or KLIOSEM®. Subjects in the study recorded the number of hot flushes per day (24-hour period) on a diary card. During the pretreatment relatively dominant estrogenic activity phase, the diary had to be completed for a minimum of 5 days in order to obtain a baseline number of hot flushes for evaluation. The subjects then received the various hormone replacement therapies for 12 months and during treatment recorded their hot flushes on the diary cards every day. For evaluation of this study, information on hot flushes recorded during the 30 days preceding the end of the study was compared with baseline to determine improvement in hot flushes as a result of treatment. Percent change from baseline to the last 30 days was calculated for 182 subjects receiving the present invention compared to 186 subjects receiving the 2 mg estradiol interrupted progestogen regimen and 188 subjects receiving the reference preparation containing 2 mg of estradiol. At 12 months, all 3 regimens showed greater than 90% reduction in the frequency of hot flushes per day. Table 1 demonstrates hot flushes from this 12-month comparative study.

TABLE 1

Vasomotor Symptoms from 12-month Comparative Study

| | Low Dosage (CP-L) Estrogen Regimen of the Present Invention 1 mg $E_2$/90 .tg NGM | High Dosage (CP-H) Estrogen Regimen 2 mg $E_2$/180 μg NGM | Kliogest ® HRT Regimen 2 mg $E_2$/ 1 mg NETA |
|---|---|---|---|
| Mean (SD) % decrease in no. of HF/day from | −94.9 (16.2) | −92.5 (22.8) | −92.8 (30.0) |
| % subjects without HF during Month 12 | 73.6 | 82.7 | 72.4 |
| Median no. days to day without HF (Kaplan-Meier Estimates) | 14 | 13 | 11 |

In Table 1, HF stands for Hot Flushes or Flashes, CP-L is the low estrogen dose of the present invention, CP-H is a 2 mg. estrogen dose regimen against which the present invention was compared. The regimen is identical to the regimen of the present invention except for the estrogen and progestogen level. $E_2$ is 17β-estradiol, NGM is norgestimate, and NETA is norethindrone acetate.

The present invention—the low dose estrogen regimen resulted in a mean decrease in the number of hot flushes per day of 94.9 % compared to baseline. The reference or Kliogest® regimen containing 2 mg of estradiol reduced hot flushes by a mean of 92.8% and the 2 mg interrupted progestogen preparation reduced hot flushes by 92.5 %. These results reveal that symptom alleviation for all regimens is more or less clinically equivalent, within reasonable statistical limits. However, it should be noted that at the lower levels of estrogen found in the regimen of the invention, the margin of safety of the preparation is thought to be markedly increased because of the reduced risk of breast cancer.

BRIEF SUMMARY OF THE DRAWINGS

In the accompanying drawings, which are used to illustrate the present invention.

DETAILED DESCRIPTION OF THE DRAWINGS

Figure 1:
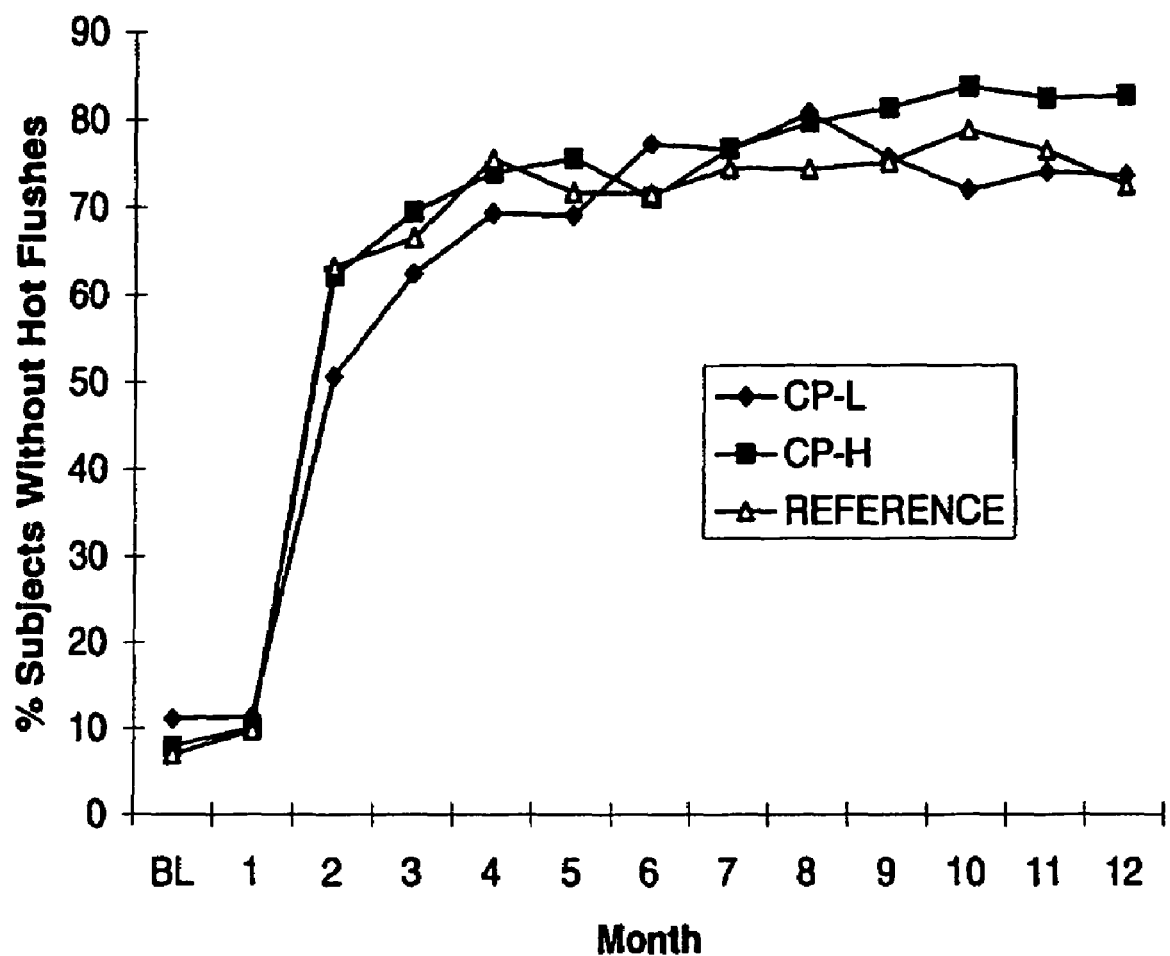
FIG. 1 is a graphical representation that plots % subjects without hot flushes by month.

In FIG. 1, the terms and associated symbols have the following meanings:

CP-L: Low Dose Regimen of the Present Invention

CP-H: High Dose Regimen of the Present Invention

Reference: Preparation sold under the Registered Trade-Mark Kliogest

Baseline (BL) data recorded during the last 30 days preceding randomization

In the Following Table 2 there are listed the number of subjects per month recorded during the last thirty days preceding randomization. This data represents the underlying data for the graphical results shown in FIG. 1.

TABLE 2

| Prep's | Month | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| | Number of Subjects | | | | | | | | | | | | |
| CP-L | 207 | 220 | 217 | 205 | 199 | 194 | 193 | 192 | 182 | 181 | 178 | 177 | 178 |
| CP-H | 203 | 218 | 209 | 190 | 169 | 147 | 135 | 133 | 123 | 118 | 117 | 114 | 110 |
| REF | 202 | 216 | 209 | 206 | 200 | 194 | 193 | 192 | 187 | 189 | 188 | 187 | 185 |

FIG. 1 shows the proportion of subjects with no hot flushes by month. It can be seen that there is an equal reduction in flushes by month 12 between the present invention containing 1 mg of estradiol and the reference preparation containing 2 mg of estradiol. The present invention did take a median of 3 days longer to reach the day without hot flushes compared to the reference preparation containing 2 mg of estradiol and one day longer compared to the 2 mg estradiol interrupted progestogen regimen.

These results are surprising since as described above, hot flushes are known to occur as a result of estrogen deficiency and estrogen replacement is the most effective treatment for preventing or improving hot flushes. In addition, it is known that progestogen administration alone is also capable of improving hot flushes [Schiff, I. The effects of progestogens on vasomotor flushes. J Reprod Med 1982; 27(Suppl):498 and Loprinzi, C L, Michalak, J C, Quella, S K, et al. Megestrol acetate for the prevention of hot flushes. N Engl J Med 1994; 331:347].

It is anticipated that a synergistic effect between the combination of estrogen and progestogen should occur to reduce hot flushes more than estrogen replacement alone. The present invention contains half as much estrogen as the two other regimens tested and at least half the progestogen. The fact that the regimen of the present invention improves hot flushes to. the same degree as the other two preparations containing at least twice as much estrogen is, therefore, unexpected and surprising.

The regimen of the present invention appears to enhance effectively estrogenic activity in some specific estrogen target tissues, such as the brain, in the case of hot flushes. This additional estrogenic effect of the present invention is supported by the observation that two estrogen-induced lipoproteins, HDL, and HDL-2, thought to be the major protective lipoproteins against coronary heart disease, are increased to the same extent by the 1 mg estradiol containing regimen of the present invention and the 2 mg estradiol containing interrupted progestogen regimen. Both regimens were superior to the reference preparation Kliogest® containing 2 mg of estradiol and 1 mg norethinedrone acetate. Since elevation in HDL-2 is thought to be an estrogen dependent effect, the fact that the same level of elevation is achieved with 1 mg of estradiol in the present invention compared to 2 mg of estradiol in a similar interrupted progestogen preparation is consistent with an unexpected estrogenic response.

The clinical relevance of the main observation relating to the vasomotor symptoms is important because the majority of women experience hot flushes at the time of menopause, and the bothersome symptoms of hot flushes are the most frequent reason for women to seek hormone replacement therapy. The improvement in hot flushes leads to long term utilization of hormone replacement therapy with many additional benefits of such use including a 50% reduction in heart disease, prevention of osteoporosis, and perhaps, as new evidence indicates, prevention of Alzheimer's disease. At the present time, the major controversial area concerning the risks of hormone replacement therapy involves breast cancer. It is believed, but not proven, that the risk of breast cancer in women taking hormone replacement therapy is related to the dose of estrogen exposure over time. The interrupted progestogen regimen used in the present invention is not likely to enhance estrogenic effects in the breast, since progestogen does not down-regulate estrogen and progestogen receptors in breast tissue (See Clarke, Christine L. and Sutherland, Robert L., Progestin Regulation of Cellular Proliferation, Endocrine Reviews, Vol. 11, 1990, No. 2, pp. 266–300).

Therefore, the receptor fluctuations, which are involved in the mechanism of action of the present invention, will not occur in the breast, and a straightforward linear estrogen effect should prevail. As a result, the present invention containing half the dose of estrogen as compared to the other two preparations containing the 2 mg of estrogen should result in an improved margin of safety with respect to breast cancer incidence while providing equivalent improvement in hot flushes seen in higher dose estrogen regimens.

While the invention has been described with particular reference to certain embodiments thereof, it will be understood that changes and modifications may be made by those of ordinary skill in the art within the scope and spirit of the following claims.

In the claims, the word "comprising" means "including the following elements (in the body), but not excluding others"; the phrase "consisting of" means "excluding more than traces of other than the recited ingredients"; and the phrase "consisting essentially of "means" excluding unspecified ingredients which materially affect the basic characteristics of the composition."

We claim:

1. A method of treating a female in need of hormone replacement therapy, the method comprising administering a medicament comprising a plurality of doses for consecutive administration in alternating phases, which phases consist of a relatively dominant estrogenic activity phase comprising three consecutive daily doses or an equivalent thereof, of a substance exhibiting estrogenic activity equivalent to about 1 mg per day of 17β-estradiol, and a relatively dominant progestogenic activity phase comprising three daily doses or an equivalent thereof, of a combination of a substance exhibiting estrogenic activity equivalent to about 1 mg per day of 17β-estradiol and a substance exhibiting progestogenic activity equivalent to about 90 µg per day of norgestimate to the female in need of treatment.

2. The method of claim 1 in which the daily doses in the relatively dominant estrogenic activity phase comprise about 1 mg per day of 17β-estradiol, and in the relatively dominant progestogenic activity phase comprise about 1 mg per day of 17β-estradiol and about 90 µg per day of norgestimate.

3. The method of claim 2 wherein the doses are in oral form.

4. The method of claim 3 wherein the doses are in tablet form.

* * * * *